United States Patent [19]

Bastart et al.

[11] Patent Number: 5,714,512
[45] Date of Patent: Feb. 3, 1998

[54] NEW COMPOSITIONS CONTAINING TAXANE DERIVATIVES

[75] Inventors: Jean-Pierre Bastart, Lesigny; Thierry Dupechez, Villemoisson Sur Orge; Jean-Louis Fabre, Paris, all of France

[73] Assignee: Rhone-Poulenc Rorer, S.A., Antony Cedex, France

[21] Appl. No.: 568,760

[22] Filed: Dec. 7, 1995

Related U.S. Application Data

[63] Continuation-in-part of Ser. No. 398,011, Mar. 3, 1995, which is a continuation-in-part of Ser. No. 930,392, Aug. 23, 1993, Pat. No. 5,403,858.

[30] Foreign Application Priority Data

Jul. 8, 1991 [FR] France .................. 91 08527

[51] Int. Cl.⁶ .................................. A61K 31/335
[52] U.S. Cl. .................. 514/449; 549/510; 514/471; 424/502
[58] Field of Search .............. 514/449; 424/502

[56] References Cited

U.S. PATENT DOCUMENTS

| | | | |
|---|---|---|---|
| 4,206,221 | 6/1980 | Miller et al. | 424/278 |
| 4,960,790 | 10/1990 | Stella et al. | 514/449 |
| 5,403,858 | 4/1995 | Bastart et al. | 514/449 |

OTHER PUBLICATIONS

B.D. Tarr, "A New Parenteral Vehicle for the Administration of Some Poorly Water Soluble Anti–Cancer Drugs," J. Parenter. Sci. Technol., 41(1), 31–33 (1987).

Merck Index, 11th ed., #7559 (1989).

*Primary Examiner*—Amelia Owens
*Attorney, Agent, or Firm*—Finnegan, Henderson, Farabow, Garrett & Dunner

[57] ABSTRACT

This invention relates to compositions containing taxane derivatives, consisting of a solution of such derivatives in a surfactant. These compositions can be used to prepare perfusion solutions.

35 Claims, No Drawings

NEW COMPOSITIONS CONTAINING TAXANE DERIVATIVES

This is a continuation-in-part of Ser. No. 08/398,011, filed Mar. 3, 1995, which is a continuation-in-part of Ser. No. 07/930,392, filed Aug. 23, 1993, now U.S. Pat. No. 5,403,858 a national phase application of PCT/FR92/00624, filed Jul. 3, 1992, hereby incorporated by reference.

The present invention relates to compositions and especially pharmaceutical dosage forms containing therapeutic agents having antitumor and antileukemic activity. It relates more especially to compositions suitable for injection containing taxane derivatives, such as, in particular, taxol or one of its analogues or derivatives of the formula (I)

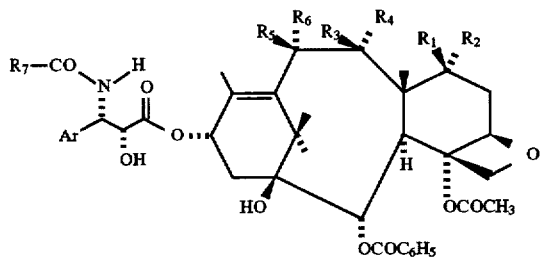

in which $R_1$ and $R_2$ each represent a hydrogen atom or one of $R_1$ and $R_2$ represents a hydrogen atom and the other represents a hydroxy, acyloxy, or acylcarbonyloxy radical, or $R_2$ represents a hydrogen atom and $R_1$ forms a single bond together with the methyl carbon atom situated in the α position, so they can form together a cyclopropane ring, one of $R_3$ and $R_4$ represents a hydrogen atom and the other represents a hydroxy radical, or $R_3$ and $R_4$ taken together form a oxo radical, $R_5$ and $R_6$ each represent each a hydrogen atom or one of $R_5$ and $R_6$ represents a hydrogen atom and the other represents a hydroxy, acyloxy, acylcarbonyloxy or a alkoxymethylcarbonyloxy radical, or $R_5$ and $R_6$ taken together form a oxo radical, $R_7$ represents an alkoxy, alkenyloxy, cycloalkyloxy or phenyl radical and Ar represents an aryl radical or preferably a phenyl radical optionally substituted by one or several atoms or radicals identical or different and selected from halogen, alkyl, alkoxy, dialkylamino, acylamino, alkylcarbonylamino or trifluoromethyl, or a 5 membered heterocyclic radical with one or more identical or different heteroatoms chosen from nitrogen, oxygen or sulfur, it being understood that alkyl radicals are straight chain or branched chain and contain 1 to 8 carbon atoms and the alkenyl radicals contain 2 to 8 carbon atoms. In one embodiment, it is preferred that when $R_2$ is a hydrogen atom and $R_1$ is a hydroxy radical, $R_3$ and $R_4$ cannot be simultaneously an oxo radical when $R_6$ is a hydrogen atom, $R_5$ is a hydroxy or acetyloxy radical, $R_7$ is a t.butoxy or a phenyl radical and Ar is a phenyl radical.

Representative taxane derivatives of the formula (I) include the following wherein $R_2$ represents a hydrogen atom and $R_1$ represents a hydrogen atom or a hydroxy radical, or $R_1$ forms a single bond together with the methyl carbon atom situated in the α position, so they can form together a cyclopropane cycle, $R_3$ and $R_4$ taken together form an oxo radical, $R_6$ represents a hydrogen atom and $R_5$ represents a hydrogen atom or a hydroxy, acetyloxy or methoxyacetyloxy radical, or $R_5$ and $R_6$ taken together form an oxo radical, $R_7$ represents a t.butoxy or a phenyl radical and Ar is a phenyl radical. In one embodiment, it is preferred that when $R_2$ is a hydrogen atom and $R_1$ is a hydroxy radical, $R_3$ and $R_4$ cannot be simultaneously an oxo radical when $R_5$ is a hydrogen atom, $R_6$ is a hydroxy or acetyloxy radical, $R_7$ is a t.butoxy or a phenyl radical and Ar is a phenyl radical.

The preferred taxane derivatives encompassed by the general formula (I) include two compounds which are known by the name of TAXOL and the name TAXOTERE.

These products exhibit in vivo substantial activity against malignant tumors, which has enabled them to be studied in the treatment of diseases resistant to other anticancer therapies.

Unfortunately, these products possess such low solubility in water that it has been necessary to prepare formulations for injection containing surfactant and ethanol. Ethanol is the best solvent for dissolving compounds of formula (I).

For example, according to the publication by Rowinsky, Lorraine, Cazenave and Donebower which appeared in the Journal of the National Cancer Institute, vol. 82, No. 15, pages 1247–1259 on 1st Aug. 1990, a first solution, termed "stock solution", containing approximately 6 mg/ml of taxol in a solvent mixture composed of:

50% by volume of ethanol
50% by volume of Cremophor EL;

is prepared. On injection, this solution is mixed with a perfusion fluid containing sodium chloride or dextrose (glucose). To obtain a mixture which is stable from both a physical standpoint and a chemical standpoint, the authors of this paper state that it is necessary to limit the concentration of active principle in the perfusion solution to concentrations of approximately 0.03 to 0.6 mg/ml (see above publication, page 1251, column 1, third paragraph).

Now, it is desirable to be able to inject sufficient doses of active principle; to this end, clinicians would like to inject concentrations of active principle of between approximately 0.3 and 1 mg/ml in the perfusion fluid; above these doses, anaphylactic shock phenomena which are difficult to control, due in the main to the Cremophor, are seen (see the publication by Rowinsky, page 1250, second column, last paragraph).

Still according to this publication, to obtain such concentrations (between 0.3 and 1 mg/ml), it is necessary to inject solutions containing, at the same time as the active principle, concentrations of each of the following compounds, ethanol and most especially Cremophor, of approximately 8 g per 100 ml of solution. Since the treatment often requires the administration of high doses of active principle, and since the concentration of the active principle, and since the concentration of the active principle in the solution is relatively low, the injection of a large volume has the effect of causing, in addition to anaphylactic manifestations, manifestations of alcohol poisoning during the treatment.

The present invention provides compositions that make it possible either to reduce the ethanol concentrations greatly, or to eliminate Cremophor and ethanol completely from the perfusions.

For this purpose, according to a first implementation of the present invention, a composition suitable for use as a stock solution is prepared, containing a compound of formula I as defined above dissolved in a surfactant which may be a polysorbate, e.g. as marketed under the name "Tween", a polyoxyethylated vegetable oil as marketed, e.g., under the name "Emulphor", polyethoxylated castor oil, also known as glycerol polyethyleneglycol ricinoleate, as marketed, e.g., under the name Cremophor preferably CREMOPHOR® EL, and virtually free from ethanol. CREMOPHOR® EL is a non-ionic solubilizer and emulsifier that can be obtained by reacting ethylene oxide with castor oil in a molar ratio of 35–40 mol ethylene oxide to 1 mol glyceride and is commercially available from BASF and has been assigned CAS Registry Number 61791-12-6. The main component of CREMOPHOR® EL is glycerol-polyethyleneglycol ricinoleate, which together with fatty acid esters of polyethylene glycol, represents the hydrophobic part of the product. The smaller, hydrophilic part consists of polyethylene glycols and ethoxylated glycerol.

The stock solution may be prepared by dissolving the active principle in ethanol, which is the best biocompatible solvent for the taxane derivatives, and then gradually adding the surfactant. Solutions containing 10 to 100 mg/ml of active principle in a mixture containing approximately 50% of surfactant can be prepared in this manner. The ethanol is then completely, or almost completely, eliminated.

To prepare, according to the present invention, the solution having a low ethanol content, the taxane derivative is dissolved in ethanol, and the surfactant, which enables micelles to be formed in containing the taxane derivative encapsulated in the surfactant after dilution in an aqueous medium, is then added. The ethanol contained in this solution is then removed at least partially by evaporation under vacuum or by any other suitable means.

According to a second method of preparing the stock solution, the taxane derivative is dissolved directly in the surfactant. According to a preferred method, a solution of surfactant containing, in particular, 1 to 2% of ethanol is prepared, and the taxane derivative is added continuously to this solution with stirring, e.g. using a helical grinder or a centrifugal disintegrator. The presence of a small amount of ethanol provides several advantages: the medium possesses a lower viscosity, and the wetting of the powder and the final filtration of the solution are improved.

The stock solution, having a low ethanol content, preferably contains less than 5% of ethanol; still more preferably, it contains less than 2% of ethanol. This solution is stable and can contain up to 200 mg/ml, preferably up to 80 mg/ml, of active principle in the surfactant.

A stock solution of taxol possesses still more preferably a concentration of between 6 and 20 mg/ml of active principle in the surfactant. This solution can be mixed, in particular to provide a final concentration of between 0.1 and 1 mg per milliliter, with the perfusion fluid, which can be physiological saline or a glucose solution. Perfusion prepared from the above stock solutions having a low ethanol content contain still more preferably between 0.3 and 0.5 mg/ml of taxol and less than 1 ml/l of ethanol.

The taxol perfusion containing the active principle without ethanol possesses a physical stability of between 8 and about one hundred hours. Physical stability is understood to mean that the solution does not exhibit any visible precipitation after 8 to 10 hours of storage at room temperature.

Taxotere; they preferably contain less than 15 ml/l of surfactant and less than 1 ml/l of ethanol.

The Taxotere perfusion containing the active principle without ethanol possesses a physical stability which can reach several months.

The taxol or Taxotere perfusions may be injected into humans at a predetermined flow rate depending on the amount of active principle it is desired to inject. The anaphylactic shock phenomena which were observed with the solutions of the prior can be avoided with these solutions.

Thus, these perfusion have made it possible to reduce, relative to the prior art, the amount of surfactant injected into humans by approximately 80% and the amount of ethanol by almost 100%.

The invention is illustrated by the following Examples.

COMPARATIVE EXAMPLE ACCORDING TO THE PRIOR ART

Taxol (0.180 g) is dissolved in ethanol (15 ml). The mixture is made to volume with Cremophor to obtain a solution (30 ml) which contains taxol (6 mg/ml).

This solution is diluted in a 5% glucose perfusion in a proportion of 1 mg/ml; the perfusion solution in a proportion of 1 mg/ml; the perfusion solution contains 87.7 ml/l of Cremophor and 87.7 ml/l of ethanol. The perfusion solution is stable for more than 21 hours.

EXAMPLES 1–7

Taxotere (32 g) is dissolved in absolute ethanol (340 ml) and Polysorbate 80 (830 g) is then added. The ethanol is evaporated off in a rotary evaporator at 30° C. at a pressure of 15 mmHg for 2 hours. The solution obtained is stable; it contains Taxotere (40 mg/ml).

After dilution is a 5% glucose perfusion solution at concentrations of 0.1, 0.3 and 0.5 mg/ml, the stability of the solutions obtained is observed.

The same method is reproduced using a solution containing Taxotere (60 mg/ml).

The same test is reproduced using taxol solutions containing taxol (12 and 20 mg/ml).

The results are shown in Table 1.

| Product | Solvent | Stock solution concentration | Active principle in the perfusion | Surfactant in the perfusion | Ethanol in the perfusion | Stability |
|---------|---------|------------------------------|-----------------------------------|-----------------------------|--------------------------|-----------|
| taxol | Polysorbate | 20 mg/ml | 1 mg/ml | 50 ml/l | <0.3 ml/l | >8 H |
| taxol | Polysorbate | 20 mg/ml | 0.3 mg/ml | 15 ml/l | <0.09 ml/l | >24 H |
| taxol | Polysorbate | 12 mg/ml | 1 mg/ml | 83.3 ml/l | <0.5 ml/l | >48 H |
| Taxotere | Polysorbate | 40 mg/ml | 0.5 mg/ml | 11.6 ml/l | 0.09 ml/l | 8 H–23 H |
| Taxotere | Polysorbate | 40 mg/ml | 0.3 mg/ml | 6.0 ml/l | 0.05 ml/l | 8 H–23 H |
| Taxotere | Polysorbate | 40 mg/ml | 0.1 mg/ml | 2.3 ml/l | 0.02 ml/l | 29 H–45 H |
| Taxotere | Polysorbate | 60 mg/ml | 0.1 mg/ml | 1.5 ml/l | <0.01 ml/l | 8 H–23 H |

A stock solution of Taxotere preferably possesses a concentration of between 20 and 80 mg/ml of active principle in the surfactant. This solution can be mixed, in particular to provide a final concentration of between 0.1 and 0.5 mg per milliliter, with the perfusion fluid, which can be a physiological saline or a glucose solution. Perfusion prepared from the above stock solutions having a low ethanol content contain still more preferably between 0.1 and 0.3 mg/ml of

EXAMPLE 8

Into a stainless steel reactor, Taxotere (258 g) is introduced and dissolved in ethanol (2425 g) with mechanical stirring for 45 minutes. Polysorbate 80 (6156 g) is added and the mixture is homogenized with mechanical stirring for 15 minutes. The solution is transferred to a reactor and the alcohol is distilled off under a reduced pressure of 10 to 50 millibars (1000 to 5000 Pa), the temperature being maintained at between 18° and 28° C. The alcohol is stilled off until its content is less than 2%.

The solution obtained is filtered through a filter having a pore size of 0.2 μm. It contains:

ethanol (1.3%)

Taxotere (39.6 mg/ml).

After dilution to mg/ml in a perfusion bag containing 5% glucose, the solution is stable without apparent precipitation for a period of more than two months.

EXAMPLE 9

Taxotere (160 mg) or taxol (160 mg) is dissolved in a mixture (10 ml) of absolute ethanol (2 ml) and Cremophor EL(218) (8 ml), and the ethanol is evaporated off in a rotary evaporator at 30° C. at a pressure of 25 mmHg for three hours. The solutions obtained are stable. They contain 20 mg/ml of Taxotere or taxol. After dilution in a 5% glucose perfusion solution at concentrations of 0.1 and 0.5 mg/ml, precipitation is observed at between 30 and 95 hours.

EXAMPLE 10

Polysorbate 80 (275.5 g) and absolute ethanol (5.4 g) are placed in a 500-ml Erlenmeyer flask, and the mixture is then stirred with a bar magnet until completely homogenized.

The solution prepared above (26.13 g) in a 50 ml flask, placed in a water bath heated beforehand and maintained throughout the test period at 30° C., is stirred at approximately 600 rpm with a bar magnet. With a spatula, Taxotere (1.076 g) is added in several portions so that the clumps disappear between two additions (the duration of the operation is approximately one hour). After incorporation of the last fraction of Taxotere, stirring is maintained until the solution becomes clear (approximately two hours).

EXAMPLE 11

4-acetoxy-2α-benzoyloxy-5β,20-epoxy-1,7β,10β-trihydroxy-9-oxo-11-taxen-13α-yl 3-t-butoxycarbonylamino-3-(2-fluorophenyl)-2-hydroxy-(2R,3S)-propionate (20 mg) is placed in round bottom flask and dissolved in absolute ethanol (0.4 ml). After dissolution, polysorbate 80 (0.5 ml) is added and the mixture is homogenized with the aid of a magnetic stirrer. The flask is placed in a vacuum using a rotary evaporator and the alcohol is distilled off under reduced pressure (10 mmHg) for one hour. The solution obtained is perfectly clear and contains 40 mg/ml of 4-acetoxy-2α-benzoyloxy-5β,20-epoxy-1,7β,10β-trihydroxy-9-oxo-11-taxen-13α-yl 3-t-butoxycarbonylamino-3-(2-fluorophenyl)-2-hydroxy-(2R,3S)-propionate. After dilution in a 0.9% aqueous sodium chloride perfusion solution to a concentration of 1 mg/ml, the solution obtained is stable for more than 24 hours.

EXAMPLE 12

4-acetoxy-2α-benzoyloxy-5β,20-epoxy-1,7β,10β-trihydroxy-9-oxo-11-taxen-13α-yl 3-t-butoxycarbonylamino-3-(4-chlorophenyl)-2-hydroxy-(2R,3S)-propionate (20 mg) was placed in a round bottomed flask and dissolved in absolute ethanol (0.4 ml). After dissolution, polysorbate 80 (0.5 ml) was added and the mixture was homogenized with the aid of magnetic stirrer. The flask was placed in a vacuum using a rotary evaporator and the alcohol was distilled off under reduced pressure (10 mmHg) for one hour. The solution obtained is perfectly clear and contains 40 mg/ml of 4-acetoxy-2α-benzoyloxy-5β,20-epoxy-1,7β,10β-trihydroxy-9-oxo-11-taxen-13α-yl 3-t-butoxycarbonylamino-3-(4-chlorophenyl)-2-hydroxy-(2R,3S)-propionate. After dilution in a 0.9% aqueous sodium chloride perfusion solution to a concentration of 1 mg/ml, the solution obtained was stable for more than 24 hours.

EXAMPLE 13

4α,10β-diacetoxy-2α-benzoyloxy-5β,20-epoxy-1β-hydroxy-7β,8β-methylene-9-oxo-19-nor-11-taxen-13α-yl 3-t-butoxycarbonylamino-2-hydroxy-3-phenyl-2-(2R,3S)-propionate (20 mg) was placed in a round bottomed flask and dissolved in absolute ethanol (0.4 ml). After dissolution, polysorbate 80 (0.5 ml) was added and the mixture was homogenized with the aid of a magnetic stirrer. The flask was placed in a vacuum using a rotary evaporator and the alcohol was distilled off under reduced pressure (10 mmHg) for one hour. The solution obtained is perfectly clear and contains 40 mg/ml of 4α,10β-diacetoxy-2α-benzoyloxy-5β,20-epoxy-1β-hydroxy-7β,8β-methylene-9-oxo-19-nor-11-taxen-13α-yl 3-t-butoxycarbonylamino-2-hydroxy-3-phenyl-(2R,3S)-propionate. After dilution in a 0.9% aqueous sodium chloride perfusion solution to a concentration of 1 mg/ml, the solution obtained was stable for more than 24 hours.

TAXOL is the compound of formula I in which Ar is unsubstituted phenyl, $R_7$ is phenyl, $R_5$ is acetyloxy, $R_6$ is hydrogen, $R_3$ and $R_4$ taken together form an oxo radical, $R_1$ is hydroxy, and $R_2$ is hydrogen, as shown below:

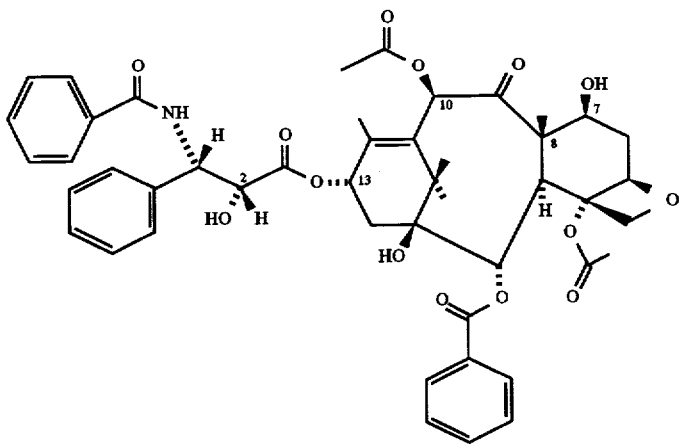

TAXOTERE is the compound of formula I in which Ar is unsubstituted phenyl, $R_7$ is t.butoxy, $R_5$ is hydroxy, $R_6$ is hydrogen, $R_3$ and $R_4$ taken together form an oxo radical, $R_1$ is hydroxy and $R_2$ is hydrogen, as shown below:

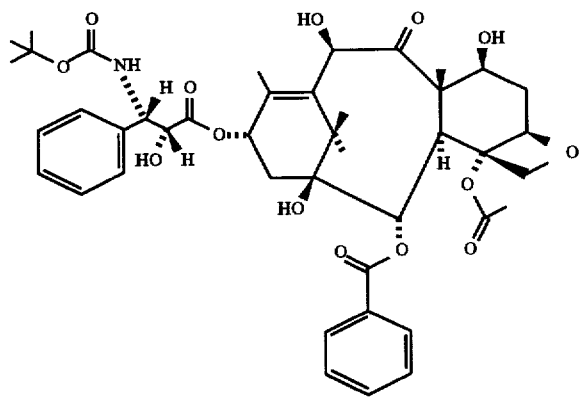

We claim:

1. A composition comprising a compound of the formula (I)

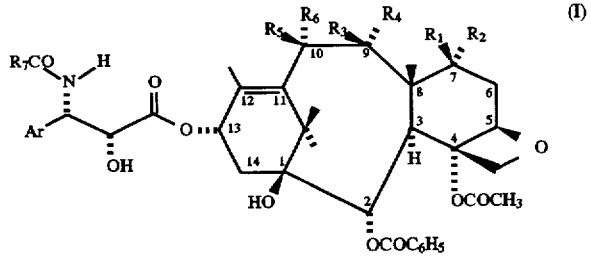

in which Ar is unsubstituted phenyl, $R_7$ is phenyl or t.butoxy, $R_6$ is hydrogen, $R_5$ is acetyloxy or hydroxy, $R_3$ and $R_4$ taken together form an oxo radical, $R_1$ is hydroxy and $R_2$ is hydrogen, said composition being dissolved in a surfactant selected from polysorbate, polyoxyethylated vegetable oil, and polyethoxylated castor oil, said composition being essentially free or free of ethanol.

2. The composition of claim 1, wherein $R_5$ is acetyloxy and $R_7$ is phenyl.

3. The composition of claim 2, wherein said surfactant is polysorbate.

4. The composition of claim 2, wherein said surfactant is polyoxyethylated vegetable oil.

5. The composition of claim 2, wherein said surfactant is polyethoxylated castor oil.

6. The composition of claim 1, wherein $R_5$ is hydroxy and $R_7$ is t.butoxy.

7. The composition of claim 6, wherein said surfactant is polysorbate.

8. The composition of claim 6, wherein said surfactant is polyoxyethylated vegetable oil.

9. The composition of claim 6, wherein said surfactant is polyethoxylated castor oil.

10. The composition of claim 1, said composition being a stock solution containing less than 5 volume % ethanol.

11. The composition of claim 10, said composition containing less than 2 volume % ethanol.

12. The composition of claim 10, said composition containing from 1 to 2 volume % ethanol.

13. The composition of claim 1, said composition containing up to 200 mg/ml of the compound of formula (I).

14. The composition of claim 13, said composition containing from 10 to 80 mg/ml of the compound of formula (I).

15. The composition of claim 14, said composition containing from 20 to 80 mg/ml of the compound of formula (I).

16. The composition of claim 13, said composition containing from 6 to 20 mg/ml of the compound of formula (I).

17. The composition of claim 13, said composition containing up to 80 mg/ml of the compound of formula (I).

18. The composition of claim 1, said composition being a perfusion containing less than 0.5 mg/ml of said compound of formula (I), less than 1 ml/l of said ethanol, and less than 15 ml/l of said surfactant.

19. The composition of claim 1, said composition being a perfusion containing less than 1 mg/ml of said compound of formula (I), and less than 1 ml/l of said ethanol.

20. The composition of claim 2, said composition being a perfusion containing 0.1 to 0.3 mg/ml of said compound of formula (I).

21. A method for preparing a composition according to claim 1, which comprises dissolving said compound of formula (I) in ethanol, adding said surfactant and removing said ethanol.

22. The method of claim 21, wherein said ethanol is removed by evaporation.

23. A method for preparing a composition according to claim 1, which comprises slowly adding said compound of formula (I) to a solution of the surfactant containing 1 to 2 volume % ethanol.

24. A stock solution comprising a compound of the formula (I)

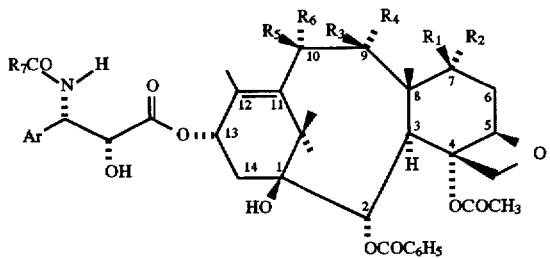

in which Ar is unsubstituted phenyl, $R_7$ is phenyl or t.butoxy, $R_6$ is hydrogen, $R_5$ is acetyloxy or hydroxy, $R_3$ and $R_4$ taken together form an oxo radical, $R_1$ is hydroxy and $R_2$ is hydrogen, said compound being dissolved in a surfactant selected from polysorbate, polyoxyethylated vegetable oil, and polyethoxylated castor oil, wherein said stock solution contains from 10 to 200 mg/ml of said compound of formula (I).

25. The stock solution of claim 24, wherein said stock solution contains from 10 to 80 mg/ml of said compound of formula (I).

26. The stock solution of claim 25, wherein said stock solution contains from 12 to 80 mg/ml of said compound of formula (I).

27. The stock solution of claim 26, wherein said stock solution contains from 20 to 80 mg/ml of said compound of formula (I).

28. The stock solution of claim 24, wherein $R_5$ is acetyloxy and $R_7$ is phenyl.

29. The stock solution of claim 28, wherein said surfactant is polysorbate.

30. The stock solution of claim 28, wherein said surfactant is polyoxyethylated vegetable oil.

31. The stock solution of claim 28, wherein said surfactant is polyethoxylated castor oil.

32. The stock solution of claim 24, wherein $R_5$ is hydroxy and $R_7$ is t.butoxy.

33. The stock solution of claim 32, wherein said surfactant is polysorbate.

34. The stock solution of claim 32, wherein said surfactant is polyoxyethylated vegetable oil.

35. The stock solution of claim 32, wherein said surfactant is polyethoxylated castor oil.

* * * * *

UNITED STATES PATENT AND TRADEMARK OFFICE
CERTIFICATE OF CORRECTION

PATENT NO. : 5,714,512

DATED : February 3, 1998

INVENTOR(S) : Jean-Pierre Bastart et al.

It is certified that error appears in the above-identified patent and that said Letters Patent is hereby corrected as shown below:

Claim 1, Column 7, Line 56, "t.butoxy" should read --tert-butoxy--;

Claim 6, Column 8, Line 24, "t.butoxy" should read --tert-butoxy--;

Claim 24, Column 9, Line 12, "t.butoxy" should read --tert-butoxy--;

Claim 32, Column 10, Line 15, "t.butoxy" should read --tert-butoxy--.

Signed and Sealed this

Twenty-first Day of September, 1999

*Attest:*

Q. TODD DICKINSON

*Attesting Officer*  *Acting Commissioner of Patents and Trademarks*

Disclaimer 5,714,512—Jean-Pierre, Bastart, Lesigny; Thierry Dupechez, Villemoisson Sur Orge; Jean-Louis Fabre, Paris, all of France. NEW COMPOSITIONS CONTAINING TAXANE DERIVATIVES. Patent Dated Feb. 3, 1998. Disclaimer filed November 8, 2007 by Assignee, Aventis Pharma S.A.

The term of this patent shall not extend beyond the expiration date of Patent No. 5,698,582.

*(Official Gazette, November 24, 2009)*